United States Patent
Foubister et al.

(12) 
(10) Patent No.: US 6,391,880 B1
(45) Date of Patent: May 21, 2002

(54) HETEROCYCLIC COMPOUNDS USEFUL AS OXIDO-SQUALENE CYCLASE INHIBITORS

(75) Inventors: Alan John Foubister; George Robert Brown; Nicholas John Newcombe, all of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/367,258

(22) PCT Filed: Feb. 9, 1998

(86) PCT No.: PCT/GB98/00406

§ 371 Date: Aug. 13, 1999

§ 102(e) Date: Aug. 13, 1999

(87) PCT Pub. No.: WO98/35959

PCT Pub. Date: Aug. 20, 1998

(30) Foreign Application Priority Data

Feb. 13, 1997 (GB) ............................................. 9702945
Jul. 26, 1997 (GB) ............................................. 9715735

(51) Int. Cl.[7] ................... A01N 43/60; S61K 31/50; C07D 403/00; C07D 239/02; C07D 401/00

(52) U.S. Cl. ................. 514/253.01; 544/295; 544/333; 544/335; 544/360

(58) Field of Search .................... 514/253.01; 544/360, 544/295, 333, 335

(56) References Cited

U.S. PATENT DOCUMENTS

| | | | |
|---|---|---|---|
| 4,167,567 A | 9/1979 | McCall ........................ | 424/250 |
| 4,231,938 A | 11/1980 | Monaghan et al. ...... | 260/343.5 |
| 4,537,896 A | 8/1985 | Claeson et al. ............. | 514/330 |
| 4,564,610 A | 1/1986 | Rahtz et al. ................ | 568/805 |
| 4,629,728 A | 12/1986 | Regnier et al. ............. | 514/252 |
| 4,788,196 A | 11/1988 | Cross et al. ................ | 514/252 |
| 4,806,536 A | 2/1989 | Cross et al. ................ | 514/252 |
| 4,835,165 A | 5/1989 | Cross et al. ................ | 514/318 |
| 4,840,963 A | 6/1989 | Shepard et al. ............. | 514/418 |
| 4,968,704 A | 11/1990 | Cross et al. ................ | 514/318 |
| 5,032,604 A | 7/1991 | Baldwin et al. ............ | 514/361 |
| 5,138,295 A | 8/1992 | Geisen et al. ............... | 544/295 |
| 5,254,563 A | 10/1993 | Huth et al. ................. | 514/292 |
| 5,332,822 A | 7/1994 | Misra .......................... | 546/164 |
| 5,364,865 A | 11/1994 | Diana .......................... | 514/318 |
| 5,371,091 A | 12/1994 | Misra et al. ................ | 514/314 |
| 5,391,556 A | 2/1995 | Heckel et al. .............. | 514/322 |
| 5,411,971 A | 5/1995 | Emonds-Alt et al. ....... | 514/318 |
| 5,556,977 A | 9/1996 | Wayne et al. .............. | 544/360 |
| 5,563,141 A | 10/1996 | Wayne et al. .............. | 514/252 |
| 5,681,954 A | 10/1997 | Yamamoto et al. ......... | 544/114 |
| 5,795,893 A | 8/1998 | Bondinell et al. .......... | 514/252 |
| 5,883,096 A | 3/1999 | Lowe et al. ................ | 514/252 |
| 5,908,843 A | 6/1999 | Gante et al. ................ | 514/255 |
| 6,022,869 A | 2/2000 | Faull ....................... | 514/227.8 |
| 6,037,343 A | 3/2000 | Ali ............................ | 514/252 |

FOREIGN PATENT DOCUMENTS

| | | |
|---|---|---|
| AU | 10177/92 | 7/1992 |
| DE | 39 05 364 A1 | 8/1990 |
| DE | 39 43 226 A | 6/1991 |
| DE | 42 43 858 A1 | 6/1994 |
| DE | 43 06 506 A1 | 9/1994 |
| EP | 0 097 630 A2 | 1/1984 |
| EP | 0 232 740 A1 | 8/1987 |
| EP | 0 233 051 | 8/1987 |
| EP | 0 244 115 | 11/1987 |
| EP | 0 308 337 | 3/1989 |
| EP | 0 324 421 A2 | 7/1989 |
| EP | 0 359 389 | 3/1990 |
| EP | 0 352 946 A1 | 10/1990 |
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 555 824 A1 | 8/1993 |
| EP | 0 576 941 A1 | 1/1994 |
| EP | 0 608 759 A2 | 8/1994 |
| FR | 2 697 252 A1 | 4/1994 |
| GB | 1 449 100 | 9/1976 |
| IE | 920095 | 7/1992 |
| WO | WO 92/08709 | 5/1992 |
| WO | WO 92/18478 | 10/1992 |
| WO | WO 93/06085 | 4/1993 |
| WO | WO 94/18185 | 8/1994 |
| WO | WO 94/20467 | 9/1994 |
| WO | WO 94/22835 | 10/1994 |
| WO | WO 96/05189 | 2/1996 |
| WO | 96 10022 | 4/1996 |
| WO | WO 96/26196 | 8/1996 |
| WO | WO 96/30343 | 10/1996 |
| WO | WO 96/33171 | 10/1996 |
| WO | 97 06802 | 2/1997 |
| WO | 97 28128 | 8/1997 |
| WO | WO 97/28129 | 8/1997 |
| WO | WO 97/29104 | 8/1997 |
| WO | WO 97/30971 | 8/1997 |
| WO | WO 98/06705 | 2/1998 |
| WO | WO 98/21188 | 5/1998 |

OTHER PUBLICATIONS

Boissier et al., "Synthesis and Pharmacological Study of New Piperazine Derivatives. I. Benzylpiperazines", J. Med. Chem., 09/1963, pp. 541–544.

(List continued on next page.)

Primary Examiner—Mukund J. Shah
Assistant Examiner—Tamthom N. Truong
(74) Attorney, Agent, or Firm—Pillsbury Winthrop LLP

(57) ABSTRACT

This invention concerns heterocyclic derivatives of formula (I) which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

11 Claims, No Drawings

OTHER PUBLICATIONS

Bowers Nemia et al., "Synthetic Routes to 3–Pyrrolidinol", Snyth. Comm., 13(13):1117–1123 (1983).

Caulkett et al., Chemical Abstracts, vol. 131:322629.

Chambers et al., "Preparation of arylpyridine compounds for treating leukotriene–related diseases", Chemical Abstracts, Abstract No. 139113, vol. 119 (1993).

Conway et al., "Approaches to the Generation of 2,3–Indolyne"; Heterocycles, 1992, 34(11) 2095–2108.

Cross et al., "Preparation of N–[(heterocyclicylmethoxy)phenyl] sulfamides and analogs as antiarrhythmics", Chemical Abstracts, Abstract No. 231211, vol. 113 (1989).

Deratani et al., "Synthesis of new dialkylaminopyridine acylation catalysts and their attachment to insoluble polymer supports", Polymer, 04/1987, pp. 825–830.

Hibino et al.; "N–Phenysulfonylindole derivatives", Chemical Abstracts, 118:147461, Apr. 1993.

Jain et al., "Compounds Acting on the Central Nervous System, VII. Studies in 1–Pyridyl–1–substituted Piperazines. A New Class of Anticonvulsants", J. Med. Chem., 09/1967, pp. 812–818.

Kataoka et al., Chemical Abstracts, vol. 123, No. 14, Oct. 2, 1995 Columbus, Ohio, US: abstract No. 179521d, "Homopiperazines as cell migration inhibitors," Xp002081582 see abstract & JP 95 145060 A (Tejin Ltd).

Kato et al., "Reactivities of 4–Chloropyridine Derivatives and Their 1–Oxides", Chem. Pharm. Bull., 15:1343–1348 (1967).

Take et al., Chemical Abstracts, vol. 133:58814.

Tawada et al., Chemical Abstracts, vol. 130:38404.

Tawada et al., Chemical Abstracts, vol. 131:170361.

Vigroux et al., "Cyclization–Activated Prodrugs: N–(Substituted 2–hydroxyphenyl and 2–hydroxypropyl)carbamates Based on Ring–Opened Derivatives of Active Benzoxasoones and Oxazolidones as Mutual Produrgs of Acetamiophen", J. Med. Chem., vol. 38, pp. 3983–3994 (1995).

Vogel et al., "Comparison of Two Experimental Thrombosis Models in Rats Effects of Four Glycosaminoglycans", Thrombosis Research, vol. 54, No. 5, pp. 399–410 (1989).

Van G. Krüger, et al; (Thomae et al.) Arzneim.–Fosch., Synthesen von N–Benzyl–aminocarbonsäuren und thren Derivaten; (Synthesis and N–benzylaminocarboxylic acids and their derivatives). vol. 23(2a), pp. 290–295.

Yokoyama et al. "Palladium–catalyzed cross–coupling reaction: direct allylation of ary bromides with allyl acetate" Tetrahedron Letters., vol. 26, No. 52—1985 pp. 6457–6460, XP002081581 Oxford GB—p. 6458–6459: compound 7.

Zaoral et al., "Amino acids and peptides. LIX. Synthesis and some biological properties of L–DABB–vasopressin", Collect. Czech. Chem. Commun., vol. 31, 1966, pp. 90–95, XPOO2081879 see compound 11, p. 95.

Kato et al., "Studies on Ketene and its Derivatives. LXXVI.[1]) Reactions of Acetoacetamide and β–Aminocrotonamide with β–Diketone, β–Ketoaldehyde and Related Compounds", Chem. Pharm. Bull., 24(2):303–309 (1976).

Kettner et al., "The Selective Inhibition of Thrombin by Peptides of Boroarginine", The Journal of Biological Chemistry, vol. 265, No. 30, pp. 18289–18297 (1990).

Kobayashi et al., Chemical Abstracts, vol. 130:296694.

Kobayashi et al., Chemical Abstracts, vol. 132:194391.

Mitsunobu et al., "Preparation of Carboxylic Esters and Phosphoric Esters by the Activation of Alcohols", Bull. Chem. Soc. Jpn., 44(12):3427–3430 (1971).

Nowak et al., Chemical Abstracts, vol. 131:337034.

Prasad et al., "Antiamoebic Action of Drugs and Synthetic Compounds Against Trophozoltes of Entamoeba Histolytica Under Axenic and Polyxenic Culture Conditions and in the Infected Rat Caecum", Curr. Sci., 08/1984, pp. 778–781.

Ratouis et al., "Synthesis and pharmacological Study of New Piperazine Derivatives, II. Phenethylpiperazines", J. Med. Chem., 01/1965, pp. 104–107.

Sato et al., "Synthetic Studies on Cardiovascular Agents. III. Synthesis of Pyrano–[2,3–c]pyrazoline Derivatives", Yakugaku Zasshi, vol. 98(3), 1978, pp. 335–348.

Saxena et al., "Quantitative Structure Activity Relationship in 3–4 Disubstituted Pyridines & I–(3"–Amino–4"–pyridyl)–4–arylpiperazines" Indian J. Chem. vol. 19B, 10/1980, pp. 873–878.

Smith et al., "Fibrin, Red Cell and Platelet Interactions in an Experimental Model of Thrombosis", Br. J. Pharmac., vol. 77, pp. 29–38 (1982).

Sundberg et al. "Synthesis with N–Protected 2–Lithioindoles"; J. Org. Chem., 1973 38(19) 3324–3330.

Szmant et al., "Concerning the Variable Character of the Sulfone Group", J. Amer. Chem. Soc., vol. 78, pp. 3400–3403 (1956).

Budaveri: Merck Index, vol. 11 Ed., 1989, See Monograph Nos. 804 and 2807.

Cattel et al: "Drug design based on biosynthetic studies: synthesis, biological activity, and kinetics of new inhibitors of 2,3–oxidosualene cyclase and squalene epoxidase.", Steroids., vol. 53, No. 3–5, 1989, pp. 363–391, XP000611661.

E. Jucker, "Über C–substituierte Piperazinederativate", Helv. Chim. Acta., 45:2383–2042 (1962).

Sartori et al., "Synthesis and analgesic activities of urea derivatives of α–amino–N–pyridyl benzene propanamide", Eur J. Med Chem (1994), 431–439.

Tabacik et al: "Squalene expoxidase, oxido–squalene cyclase and cholesterol biosynthesis in normal and tumoral mucosa of the human gastrointestinal tract. Evidence of post–HMGCoA regulation.", Biochim. Biophys. Acta, vol. 666, No. 3, 1982, pp. 433–441, XP000610864.

Wallis, "Inhibitors of Coagulation Factor Xa: From Macromolecular Beginnings to Small Molecules", Current Opinion in Therapeutic Patents, Aug., 1993, pp. 1173–1179.

HETEROCYCLIC COMPOUNDS USEFUL AS OXIDO-SQUALENE CYCLASE INHIBITORS

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

There is evidence that high serum cholesterol levels are an important risk factor in coronary heart disease and associated diseases such as atherosclerosis and ischaemic heart disease. As a result there has been a great deal of interest in finding ways of lowering cholesterol levels in blood plasma. Although it has been possible to obtain sonic reduction by means of diet, only modest reductions have been obtained by controlling the dietary intake of cholesterol. Consequently, there is a need for therapeutic approaches to reducing cholesterol levels.

Several different classes of compounds have been reported to possess the ability to lower cholesterol levels in blood plasma. For example agents which inhibit the enzyme HMGCoA reductase, which is essential for the production of cholesterol, have been reported to reduce levels of serum cholesterol. Illustrative of this class of compounds in the HMGCoA reductase inhibitor known as lovastatin which is disclosed in U.S. Pat. No. 4,231,938. Other agents which are reported to lower serum cholesterol include those which act by complexing with bile acids in the intestinal system. This results in a lowering of the levels of bile acid circulating in the enteroheptatic system and promotes replacement of bile acids by synthesis in the liver from cholesterol. In turn this results in an upregulation of the hepatic LDL cholesterol receptor and in a lowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interupt cholesterol biosynthesis and give rise to a lowering of cholesterol levels in blood plasma.

The present invention is based on the discovery that certain heterocyclic derivatives arc inhibitors of oxido-squalene cyclase and are hence useful in treating diseases and medical conditions in which inhibition of oxido-squalene cyclase is desirable.

According to the present invention there is provided compounds of formula I (set out hereinafter together with the other formulae referred to herein in a separate sheet following the Examples), or a pharmaceutically-acceptable salt thereof, wherein:

G is selected from CH and N;

$T_1$ is selected from N and CR, wherein R may be hydrogen, (1–4C)alkyl, (2–4C)alkenyl and (2–4C)alkynyl, (preferably R is hydrogen);

$R_1$ is hydrogen, amino, halogeno, cyano, nitro, carboxy, (1–6C)alkanoyl, (1–6C)alkyl, (1–6C)alkoxy, N-(1–6C) alkylamino, N,N-di-[(1–6C)alkyl]amino. (1–6C) alkylthio, (1–6C)alkylsulphinyl and (1–6C) alkylsulphonyl;

m is 1 or 2;

A is selected from (1–4C)alkylene, carbonyl or (1–4C) alkylcarbonyl, (preferably A is (1–4C)alkylcarbonyl or carbonyl);

$T_2$ is selected from CH and N;

$T_3$ is selected from N and CR, wherein R is as defined above, (preferably R is hydrogen);

provided that when $T_2$ is CII then $T_3$ is not CR and when $T_1$ is CR then $T_3$ is not CR;

a and b are independently selected from 2 and 3;

c and d are independently selected from 1 and 2;
wherein the ring containing $T_1$ and the ring containing $T_2$ may, independently, be optionally substituted by one or more substituents selected from (1–6C)alkyl, (1–6C)alkoxy, phenyl(1–4C)alkyl, halogeno and (1–6C)alkoxycarbonyl;

X is selected from oxy, thio, sulphinyl, sulphonyl, carbonyl, carbonylamino, N-(1–6C) alkylcarbonylamino, sulphonylamino, methylene, (1–4C)alkymethylene and di-(1–6C)alkylmethylene, and when $T_2$ is CH, X may also be selected from aminosulphonyl and oxycarbonyl;

Q is selected from (5–7C)cycloalkyl, a heterocyclic moiety containing up to 4 heteroatoms selected from nitrogen oxygen and sulphur phenyl, naphthyl, phenyl (1–4C)alkyl and phenyl(2–6C)alkenyl, and wherein the last three groups may optionally bear a phenyl substituent;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C) alkoxy, (3–6C)cycloalkyl, (3–6C)cycloalkyl(1–4C) alkyl, (1–4C)alkylenedioxy, (1–6C)alkylamino, di-[(1–6C)alkyl]amino, N-(1–6C(alkylcarbamoyl, di-N-[(1–6C)alkyl]carbamoyl, (1–6C) alkanoylamino, (1–6C)alkoxycarbonyl, (1–6C) alkylthio, (1–6C)alkylsulphinyl, (1–6C) alkylsulphonyl, halogeno(1–6C)alkyl, (1–6C) alkanoyl, tetrazolyl and a heteroaryl group comprising a 5- or 6-membered monocyclic ring containing up to three heteroatoms selected from nitrogen, oxygen and sulphur.

The compounds of the present invention arc oxido-squalene cyclase inhibitors and hence possess the property of inhibiting cholesterol biosynthesis. There is provided as a feature of the invention a compound of formula I, or a pharmaceutically-acceptable salt thereof, for use as a medicament. Accordingly, there is also provided the use of a compound of formula I, or a pharmaceutically acceptable salt thereof, for the manufacture of a medicament for inhibiting cholesterol biosynthesis. Thus the compounds of the present invention will be useful in treating diseases or medical conditions in which an inhibition of oxido-squalene cyclase is desirable, for example those in which a lowering of the level of cholesterol in blood plasma is desirable. In particular, the compounds of the present invention will be useful in treating hypercholesterolemia and/or ischaemic diseases associated with atheromatous vascular degeneration such as atherosclerosis. As inhibitors of cholesterol biosynthesis, the compounds of the present invention will also be useful in treating fungal infections.

Thus according to a further feature of the present invention there is provided a method of inhibiting oxido-squalene cyclase in a warm-blooded animal (such as man) requiring such treatment, which method comprises adminstering to said animal an effective amount of a compound of formula I, or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

In particular, the compounds of the present invention are potentially useful in inhibiting cholesterol biosynthesis in man and hence in treating the above-mentioned medical conditions in man.

It will be understood that when compounds of formula I contain a chiral centre, they may exist in, and be isolated in, optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art, for example by, resolution of a racemic form, by synthesis from optically active starting materials or by asymmetric synthesis. It will be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "tert-butyl" being referred to specifically when intended.

A particular value for A when it is (1–4C)alkylene is, for example, methylene, ethylene, trimethylene or tetramethylene, preferably methylene.

A particular value for X when it is a N-(1–4C)alkylcarbonylamino group is, for example, N-methylcarbonylamino or N-ethylcarbonylamino; when it is (1–4C)alkylmethylene is, for example, ethane-1,1-diyl or propane-1,1-diyl; and when it is di-(1–4C)alkylmethylene is, for example, propane-2,2-diyl. It is also to be understood that when X is a carbonylamino or N-(1–4C)alkylcarbonylamino group, it is the carbonyl group therein which is attached to $T_2$. Likewise when X is a sulphonylamino group it is the sulphonyl group therein which is attached to $T_2$ whereas, when X is an aminosulphonyl group, the sulphonyl group therein is attached to Q.

A particular value for Q when it is naphthyl is, for example, 1-naphthyl or 2-naphthyl.

A particular value for Q when it is phenylalkyl is, for example, phenyl(1–2C)alkyl, such as benznyl, 2-phenylethyl or 1-phenethyl.

A particular value for Q when it is phenylalkenyl is, for example, phenyl(2–4C)alkenyl such as styryl, cinnamyl or 3-phenylprop-2-enyl.

A particular value for Q when it is a heterocyclic moiety is a 5- or 6-membered heterocyclic moiety, which is a single ring or is fused to one or two benzo rings, such as furyl, benzofuranyl, tetrahydrofuryl, chromanyl, thienyl, benzothienyl, pyridyl, piperidino, quinolyl, 1,2,3,4-teirahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imnidazolyl, benzimidazolyl, pyrazolyl, indazolyl, oxazolyl, benzoxazolyl, isoxazolyl, thiazolyl, benzothiazolyl, isothiazolyl, morpholino, 4$\underline{H}$-1,4-benzoxazinyl, 4$\underline{H}$-1,4-benzothiazinyl, 1,2,3-triazolyl. 1,2,4-triazolyl, oxadiazolyl, furazanyl, thiadiazolyl, tetrazolyl, dibenzofuranyl and dibenzothienyl, which may be attached to X through any available position including, for an appropriate X group such as carbonyl and methylene, through any available nitrogen atom.

A particularly preferred value for Q when it is heterocyclic moiety is a 5- or 6-membered monocyclic heteroaryl ring such as furyl, thienyl, pyridyl, pyrazinyl, pyrimidinyl, pyridazinyl, pyrrolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached to X through any available position including, for an appropriate X group such as carbonyl and methylene, through any available nitrogen atom.

A particular value for Q when it is cycloalkyl is, for example, cyclopentyl and cyclohexyl.

Particular values for $R_1$ include, for example

| | |
|---|---|
| for halogeno; | chloro, bromo, iodo or fluoro; |
| for alkyl; | (1–4C)alkyl, such as methyl, ethyl, propyl, iso-propyl, butyl, iso-butyl, sec-butyl or tert-butyl; |
| for alkoxyl; | methoxy, ethoxy, propoxy, isopropoxy, butoxy, pentoxy or 3-methylbutoxy; |
| for alkoxy-carbonyl; | (1–4C)alkoxycarbonyl, such as, methoxycarbonyl, ethoxycarbonyl, propoxycarbonyl, iso-propoxy-carbonyl, butoxycarbonyl or tert-butoxycarbonyl; |
| for halogeno alkyl | halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl; |
| for alkanoyl; | formyl, acetyl, propionyl and butyryl. |

Particular values for optional substituents on the ring containing $T_1$ include, for example,

| | |
|---|---|
| for alkyl; | (1–4C)alkyl such as methyl, ethyl propyl, iso-propyl, butyl, iso-butyl, sec-butyl or tert-butyl; |
| for alkenyl; | (2–4C)alkenyl, such as allyl, prop-1-enyl, 2-methyl-2-propenyl or 2-butenyl; |
| for alkynyl; | (2–4C)alkynyl, such as prop-2-ynyl or but-2-ynyl. |

Particular values for optional substituents on the ring containing $T_2$ include, for example,

| | |
|---|---|
| for alkyl; | (1–4C)alkyl such as methyl, ethyl, propyl, iso-propyl, butyl, iso-butyl, sec-butyl or tert-butyl; |
| for alkoxy; | (1–4C)alkoxy such as methoxy, ethoxy, propoxy, iso-propoxy or butoxy; |
| for phenylalkyl; | phenyl (1–2C)alkyl such as benzyl, 2-phenylethyl or 1-phenylethyl |

-continued

| | |
|---|---|
| for halogeno; | fluoro, chloro, bromo or iodo |
| for alkoxycarbonyl; | methoxycarbonyl, ethoxycarbonyl, iso-propoxycarbonyl or butyoxycarbonyl; |

Particular values for optional substituents which may be present on Q include, for example,

| | |
|---|---|
| for alkyl; | (1–4C)alkyl, such as methyl, ethyl, propyl, iso-propyl, butyl, iso-butyl, sec-butyl or tert-butyl; |
| for cycloalkyl | cyclopropyl, cyclobutyl or cyclopentyl; |
| for cycloalkylalkyl | (3–6C)cycloalkyl(1–2C)alkyl such as cyclopropylmethyl, cyclopropylethyl, cyclobutylmethyl or cyclopentylmethyl; |
| for alkenyl; | (2–4C)alkenyl such as allyl, prop-1-enyl, 2-methyl-2-propenyl or 2-butenyl; |
| for alkynyl; | (2–4C)alkynyl, such as prop-2-ynyl or but-2-ynyl; |
| for alkoxy; | (1–6C)alkoxy, such as methoxy, ethoxy, propoxy, iso-propoxy, butoxy, pentoxy or 3-methylbutoxy; |
| for alkylamino; | (1–4C)alkylamino, such as methylamino, ethylamino, propylamino or butylamino; |
| for di-alkylamino; | di-[(1–4C)alkyl]amino such as dimethylamino, diethylamino, methylpropylamino or dipropylamino; |
| for alkyl-carbamoyl; | (1–4C)alkylcarbamoyl such as N-methylcarbamoyl, N-ethylcarbamoyl, N-propylcarbamoyl, N-butylcarbamoyl or N-tert-butylcarbamoyl or (N-(2-methylpropyl)-carbamoyl; |
| for di-alkyl-carbamoyl; | di-[(1–4C)alkyl]carbamoyl, N,N-dimethylcarbamoyl or N,N-diethylcarbamoyl; for |
| alkoxy-carbonyl; | (1–4C)alkoxycarbamoyl such as methoxycarbonyl, ethoxycarbonyl, propoxycarbonyl, iso-propoxycarbonyl, butyoxycarbonyl or tert-butoxycarbonyl; |
| for alkylthio; | (1–4C)alkylthio such as methylthio, ethylthio, propylthio) iso-propylthio or butylthio; |
| for alkyl-sulphinyl; | (1–4C)alkylsulphinyl such, as methylsulphinyl, ethyl-sulphinyl, propylsulphinyl, iso-propylsulphinyl or butylsulphinyl; |
| for alkyl-sulphonyl; | (1–4C)alkylsulphonyl such as methylsulphonyl, ethylsulphonyl, propylsulphonyl, iso-propylsulphonyl or butylsulphonyl; |
| for halogeno; | fluoro, chloro, bromo or iodo; |
| for halogenoalkyl; | halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluromethyl, difluoromethyl and fluoromethyl; |
| for alkanoylamino; | (1–4C)alkanoylamino such as formamido, acctamido, propionamido, isopropionamido, butyramido and iso-butyramido: |
| for alkylenedioxy; | methylenedioxy or ethylenedioxy; |
| for alkanoyl; | (1–4C)alkanoyl such as formyl, acetyl, propionyl or butyryl. |

In general, it is preferred that $R_1$ is hydrogen, amino, (1–6C)alkyl, (1–6C)alkoxy, N-(1–6C)alkylamino, N,N-di [(1–6C)alkyl]amino, (1–6C)alkylthio, (1–6C)alkylsulphinyl and (1–6C)alkylsulphonyl.

In general, it is preferred that X is methylene, thio, carbonyl or sulphonyl.

In general, the heterocyclic rings containing $T_1$ and $T_2$ will be unsubstituted or bear one or two substituents selected from those hereinbefore defined.

In general, Q will be unsubstituted or will bear one, two or three (preferably one or two) substituents selected from those hereinbefore defined.

In general, it is preferred that A is carbonyl.

In general, it is preferred that a=b=c=d=2.

In general it is preferred that when $T_2$ is N, X is selected from methylene. carbonyl and sulphonyl, when $T_2$ is CH, X is selected from thio and carbonyl.

In general it is preferred that Q is phenyl, naphthyl or phenyl(2–6C)alkenyl (such as styryl) or a heteroaryl group as herein before defined (such as thienyl).

A value of X of particular interest is sulphonyl.

Specific values for optional substituents on the ring containing $T_2$ include, for example (1–6C)alkyl (such as methyl) and (1–6C)alkoxycarbonyl (such as methoxycarbonyl or ethoxycarbonyl).

Specific values for optional substituents for Q include, for example, halogeno (such as fluoro, chloro, bromo or iodo), (1–6C)alkoxy (such as methoxy, or ethoxy), (1–6C)alkyl (such as methyl, iso-propyl or t-butyl), halogeno(1–6C)alkyl (such as trifluoromethiyl), di-[(1–4C)alkyl]amino (such as dimethylamino), nitro, cyano, (1–6C)alkyl (such as methyl, ethyl, propyl or butyl), (1–6C)alkanoylamino (such as acetylamino) and pyridyl.

Specific values for a, b, c and d include, for example, a=2, b=2, c=2 and d=2 or a=2, b=3, c=2 and d=2.

Specific values for $R_1$ include for example, hydrogen, amino, (1–6C)alkyl (such as methyl and halogeno (such as chloro).

Specific values for Q—X— include, for example, phenyl-$CH_2$—, phenyl-CO—, phenyl-$SO_2$, phenyl-S, naphthyl-$CH_2$—, naphthyl-CO—, naphthyl-$SO_2$—, naphthyl-S— and styryl-$SO_2$—. Further specific values include thienyl-$SO_2$.

Values of Q—X— of particular interest include, for example, phenyl-$SO_2$—, phenyl-CH=$CHSO_2$—, naphthyl-S—, benzyl- and naphthyl-$SO_2$—; wherein the phenyl or naphthyl moiety may be unsubstituted or may optionally bear one or more (preferably one or two) substituents selected from those hereinbefore defined.

In a particular embodiment, the heterocyclic rings containing $T_1$ and $T_2$ are unsubstituted.

Particular embodiments of the present invention include the following in which G, a, b, c, d, $R_1$, m, $T_1$, $T_2$, $T_3$, A, X and Q may take any of the values mentioned above unless stated otherwise:

(i) G is CH;

(ii) a, b, c and d are each 2;

(iii) G is CH or N, $T_1$, is CH. $T_2$ and $T_3$ are N;

(iv) G is CH or N, $T_1$ is CH, $T_2$ and $T_3$ are N, X is oxy, thio, sulphinyl or sulphonyl;

(v) G is CH or N, $T_1$ is CH, $T_2$ and $T_3$ are N, X is carbonyl, carbonylamino or sulphonylamino;

(vi) G is CH or N, $T_1$ is CH, $T_2$ and $T_3$ are N, X is methylene, (1–4C)alkymethylene or di-(1–6C) alkylmethylene, (vii) G is CH or N, $T_1$ is CH, $T_2$ and $T_3$ are N, X is sulphonyl;

(viii) G is CH or N, $T_1$ is CH, $T_2$ and $T_3$ are N, X is sulphonyl Q is phenyl;

(viv) G is CH or N, $T_1$ is CH, $T_2$ and $T_3$ are N, X is sulphonyl Q is heteroaryl; or (ix) G is CH or N, $T_1$ is CH, $T_2$ and $T_3$ are N, X is sulphonyl Q is naphthyl;

Compounds of particular interest include, for example, those in which X is sulphonyl. A is a direct bond, a=b=c= d=2, $R_1$ and m are as hereinbefore defined and $T_1$, $T_2$, $T_3$ and Q are as defined in any one of the following group (i) $T_1$ is CH, $T_2$ is CH; $T_3$ is N and Q is phenyl;

(ii) $T_1$ is CH, $T_2$ is CH, $T_3$ is N and Q is phenyl(2–6) alkenyl such as styryl;

(iii) $T_1$ is CH, $T_2$ is CH, $T_3$ is N and Q is naphthyl;

(iv) $T_1$ is N, $T_2$ is N, $T_3$ is N and Q is phenyl;

(v) $T_1$ is N, $T_2$ is N, $T_3$ is N and Q is phenyl(2–6C)alkenyl such as styryl; or (vi) $T_1$ is N, $T_2$ is N, $T_3$ is N and Q is naphthyl;
and in each of the above Q and the rings contain $T_1$ and $T_2$ are optionally substituted as hereinbefore defined.

In a further group of preferred compounds are compounds of formula Ia wherein G is CH or N (preferably CH), $T_1$ is CH, $T_2$ is N, A is carbonyl or (1–4C)alkylene (preferably a direct bond), X is selected from methylene, thio, carbonyl and sulphonyl (preferably sulphonyl) and Q is selected from phenyl and phenyl(2–6C)alkenyl; and wherein the rings containing $T_1$ and $T_2$ are each independently unsubstituted or bear one or two substituents selected from those hereinbefore defined and Q is phenyl which is unsubstituted or bears one or two substituents independently selected from those hereinbefore defined.

In a further group of compounds of formula Ia G is CH (preferably CH), $T_1$ is N or CH, A is carbonyl, $T_2$ is N, X is methylene, carbonyl or sulphonyl (preferably sulphonyl) and Q is naphthyl which may be unsubstituted or may optionally bear one or two substituents selected from those hereinbefore defined.

In a further group of compounds of formula Ia G is CH or N (preferably CH), $T_1$ is N or CH (preferably CH). A is carbonyl. $T_2$ is CH, X is thio or carbonyl and Q is phenyl or naphthyl, which may be unsubstituted or may bear one or two substituents selected from those hereinbefore defined.

In a further group of compounds of formula Ia G is CH or N (preferably CH). $T_1$ is CH. $T_2$ is CH or N (preferably N). A is carbonyl. Q—X— is selected from phenyl-SO$_2$—, phenyl-CH=CHSO$_2$—, naphthyl-S—, benzyl- and naphthyl-SO$_2$—; wherein the phenyl or naphthyl moiety may be unsubstituted or may, optionally bear one or more (preferably one or two) substituents selected from those hereinbefore defined; and the heterocyclic rings containing $T_1$ and $T_2$ are unsubstituted.

In a further group of compounds of formula Ia G is N or CH (preferably CH) $T_1$ is CH, A is carbonyl or (1–2C) alkylene (preferably a direct bond). $T_2$ is N, X is methylene, thio, carbonyl or sulphonyl (preferably sulphonyl); and Q is selected from phenyl or naphthyl which may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C:)cycloalkyl, (3–6C)cycloalkyl(1–4C) alkyl, (1–4C)alkylenedioxy, (1–6C)alkylamino, di-[(1–6C) alkyl]amino, N-(1–6C)alkylcarbamoyl, di-N[(1–6C)alkyl] carbamoyl), (1–6C)alkanoylamino, (1–6C)alkoxycarbonyl, (1–6C)alkylthio, (1–6C)alkylsulphinyl, (1–6C) alkylsulphonyl, halogeno(1–6C)alkyl, (1–6C)alkanoyl and tetrazolyl; and the heterocyclic rings containing $T_1$ and $T_2$ are unsubstituted.

In a specific embodiment G is CII, a=b=c=d=2, the rings containing $T_1$ and $T_2$ are unsubstituted, A is carbonyl, X is sulphonyl, Q is an optionally substituted (as hereinbefore defined) phenyl, naphthyl, phenyl(2–6C)alkenyl or a 5- or 6-membered heteroaryl moiety. In the above, Q is preferably unsubstituted or substituted by one or two halogen groups.

Compounds of special interest include those described in the accompanying examples and their pharmaceutically acceptable salts and are hence provided as a further feature of the present invention.

The compounds of formula I and Ia and their pharmaceutically acceptable salts may be prepared by processes known to be applicable to the preparation of structurally related compounds. These procedures are illustrated by the following representative processes in which the various groups and radicals such as m, $R^1$, a, b, c, d, G, $T_1$, A, $T_2$, $T_3$, X and Q are as hereinbefore defined (unless stated otherwise), and are provided as a further feature of the present invention.

(a) When $T_3$ is N and A is carbonyl or alkylcarbonyl, reacting a compound of formula II, or a reactive derivative of the carboxylic acid group, with an amine of formula III.

A suitable reactive derivative of an acid of formula II is, for example, an acyl halide such as an acyl chloride formed by the reaction of the acid with an inorganic acid chloride such as thionyl chloride. Further suitable reactive derivatives include a mixed anhydride such as an anhydride formed by the reaction of the acid with a chloroformate such as isobutyl chloroformate: an active ester such as an ester formed by the reaction of the acid and a phenol such as pentafluorophenyl, an ester such as pentafluorophenyl trifluoroacetate or an alcohol such as N-hydroxybenzotriazole or N-hydroxysuccinimide, an acylazide, for example an azide formed by the reaction of the acid and an azide as dephenylphosphoryl azide; an acyl cyanide, for example a cyanide formed by the reaction of an acid and a cyanide such as diethylphosphoryl cyanide, or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylaminolithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an ad arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylamiiinopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The compounds of formula II where $T_1$ is CH may be prepared as shown in Scheme 1(a) and where $T_1$ is N as shown in Scheme 1(b). The ester obtained may be hydrolysed to the acid and then converted to a reactive derivative such as the acyl chloride using standard methodology.

(b) For the preparation of compounds of formula I in which $T_2$ is N, reacting an amine of formula IV, with a compound of formula Z—X—Q in which Z is a displaceable group.

The reaction will, in general, be conveniently carried out in the presence of a suitable base. Suitable bases are those mentioned in (a) above.

A suitable value for the displaceable group Z is, for example a halogeno or sulphonyloxy group, for example a fluoro, chloro, bromo, mesyloxy or 4-tolylsulphonyloxy group.

The reaction is conveniently performed in a suitable inert solvent or diluent as defined hereinbefore and at a temperature in the range, for example, 0° to 150° C. conveniently at or near ambient temperature.

(c) For the preparation of a compound of formula I in which $T_1$ is N, and wherein A is a carbonyl, reacting a compound of formula V with an acid of formula VIII or a reactive derivative thereof.

The reaction will, in general, be carried out in the presence of a suitable base as mentioned in (a) above.

The reaction is conveniently performed in a suitable inert solvent or diluent as defined hereinbefore and at a temperature in the range, for example 0° to 150° C., conveniently at or near ambient temperature.

(d) For the preparation of a compound of formula I in which A is (1–4)alkylene reducing a compound of formula I wherein A is carbonyl, to produce a compound of formula I in which A is methylene, or wherein A is (1–3C) alkylcarbonyl, to produce a compound of formula I in which A is (2–4C)alkylene.

Suitable agents to effect the reduction include borane complexes, such as borane dimethylsulphide, and complex metal hydrides, such as aluminum lithium hydride. The reaction with, in general, be conveniently carried out in a suitable inert solvent, such as tetrahydrofuran or diethylether, and at a temperature range of from 0 to 25° C.

The starting materials referred to in the above processes may be prepared by chemical routes well known to those skilled in the art.

Compounds of formula V may be prepared by standard methodologies such as shown in Scheme 1(b).

Compounds of formula V in which G is CH may be prepared by reduction of the corresponding bipyridyl derivative using, for example, hydrogen in the presence of a catalyst such as a precious metal catalyst and under pressure. Typically, a catalyst of platinum oxide (Adams catalyst) may be used and a pressure of 10 to 200 atmospheres. A solvent is usually employed such is an aqueous mineral acid (for example, 2M hydrochloric acid).

Alternatively, and preferably, compounds of formula V in which G is CH may be prepared by reduction of the corresponding bipyridyl derivative using hydrogen in the presence of a rhodium catalyst in a non-acidic aqueous solvent at a pressure of around 10 atmospheres.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups are mentioned under (a) above. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminum trichloride) under Friedel Crafts conditions; the introduction of an alkyl group using an alkyl halide and Lewis acid (such as aluminum trichloride) under Fiedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I or Ia is required, it may be obtained, for example, by reaction of said compound with the appropriate acid (which affords a physiologically acceptable anion), or with the appropriate base (which affords a physiologically acceptable cation), or by an other conventional salt formation procedure.

When an optically active form of a compound of the formula I is required, it may be obtained, for example, by carrying out one of the aforesaid procedures using an optically active starting material or by resolution of a racemic form of said compound using a conventional procedure.

The beneficial pharmacological properties of the compounds of the present invention may be demonstrated using one or more of the following techniques (a) In Vitro Test to Measure Inhibition of Oxido-Squalene Cyclase This test measures the inhibition of microsomal oxido-squalene cyclase in vitro by compounds at set concentrations in the incubation medium.

Microsomes are prepared from rat liver according to methods known in the art, for example, the method described in published European Patent Application No 324,421 and stored in liquid nitrogen prior to assay. Assay vials are kept at 37° C. throughout the incubation. The microsomes typically contain 15–20 mg of protein per ml of microsomes. For assay, 1 ml of microsomes are diluted by the addition of 722 µl of 50 mM phosphate buffer pH 7.4.

Phosphate buffered Tween 80 (polyoxyethylene sorbitan monolaurate) is prepared by adding 0.1 g Tween 80 to 100 ml of 50 mM phosphate buffer.

A stock solution of oxido-squalene is made up as a solution in ethanol (0.65 mg. ml.$^{-1}$). 18 µl of radio-labelled oxido-squalene (1 µCi.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a $10^{-4}$M stock solution. Dilutions are made from the stock to give $10^{-5}$M, $10^{-6}$M etc.

Phosphate buffered Tween 80 (28 µl) is placed in 5 ml disposable plastic vials and 4 µl of the solution of the test compound is added and mixed well. An aliquot of the oxido-squalene mix (15 µl) is added and the vials pre-incubated for 10 minutes at 37° C. A portion of the microsomes (14.6 µl) are then added and incubated for a further 1 hour. The reaction is stopped by the addition of 315 µl of a mixture of 16% KOH in 20% ethanol.

The samples are then placed in a water bath at 80° C. for 2 hours to saponify. At the end of this process water (630 µl) is added followed by hexane (5 ml). The samples are tumble mixed for 5 minutes and then centrifuged. The hexane phase is removed and evaporated under nitrogen. The samples are then reconstituted in 300 µl of a 80:20 mixture of a acetonitrile:isopropyl alcohol. The samples are then chromatographed using a Hichrom 30DsS1 column with an isocratic elution using a 95:5 mixture of acelonitrile:isopropyl alcohol and a flow rate of 1 ml.min$^-$$_1$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

By way of example, the compound described in Example 2 gave about 94% inhibition of rat microsomal oxido-squalene cyclose at a concentration of 0.1 µM.

(b) In Vivo Test to Measure Inhibition of Oxido-Squalene Cyclase

The ability of a compound to inhibit oxido-squalene cyclase and/or inhibit cholesterol biosynthesis may be assessed by a routine laboratory procedure carried out in the rat. The test involves administration of the compound to rats on a reversed lighting regimen. Female rats (35–55 g) are housed in reverse lighting conditions (red light from 0200 h–1400 h) for a period of about 2 weeks prior to test. Animals are allowed free access to chow and drinking water throughout this period. At test, animals should weigh 100–140 g. The rats are dosed orally with the compound (typically 10–50 mg/kg) formulated in apolyethylene glycol/hydroxypropylmethyl cellulose mix. After 1 hour the rats are given triturated sodium mevalonate (15 µCi/kg) intraperitoneally. Two hours after administration of the compound the rats are terminated and a piece of liver removed and weighed. The tissue is saponified at 80° C. for 2 hours in an ethanolic/potassium hydroxide solution (80% w/v aqueous KOH diluted 1:10 with ethanol). Water (2 ml) is added and the mixture extracted with iso-hexane (2×5 ml). The organic extracts are combined, evaporated to dryness under a stream of nitrogen and the residue is dissolved in a mixture of acetonitrile/iso-propanol (300 µl). An aliquot (200 µl) of this solution is loaded onto a HPLC column to separate the sterols. The radio-label content of each fraction is assessed using a radio chemical flow detector. Inhibitors of oxido squalene cyclase are classed as those compounds which caused a build up of substrate and a concomitant disappearance of cholesterol and its precursors. $ED_{50}$ values are generated in the usual manner.

By way of example, the compound described in Example 2 below gave about 85% inhibition of rat cholesterol biosynthesis when dosed at 2 mg/kg.

No overt toxicity was detected when compounds of formula I were adminstered at several multiples of their minimum inhibitory dose or concentration.

The compounds of the present invention will be useful in treating diseases or medical conditions in which an inhibition of choleserol biosynthesis or lowering of cholesterol levels in blood plasma is desirable, for example, hypercholesterolemia and/or ischaemic diseases associated with atheromatous vascular degeneration such as atherosclerosis.

When used in the treatment of diseases and medical conditions such as those mentioned above it is envisaged that a compound of formula I or a pharmaceutically acceptable salt thereof, will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I, or a pharmaceutically-acceptable salt thereof, will usually be administered in the form of a pharmaceutical composition, that is together with a pharmaceutically-acceptable diluent or carrier, and such a composition is provided as a further feature of the present invention.

A pharmaceutical composition of the present invention may be presented in a variety of dosage forms. For example, it may be in the form of tablets, capsules, solutions or suspensions for oral administration, in the form of suppository for rectal administration, in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I, or a pharmaceutically-acceptable salt thereof, in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

The invention will now be illustrated by the following non-limiting Examples in which, unless otherwise stated:

(i) evaporations were carried out by rotary evaporation in vacuo;

(ii) operations were carried out at room temperature, that is in the range 18–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz using tetramethylsilane (TMS) as an internal standard, and are expressed as chemical shifts (delta values) obtained in DMSO-$d_6$ (unless stated otherwise) in parts per million relative to TMS using conventional abbreviations for designation of major peaks: s, singlet, m, multiplet; t, triplet; br, broad; d, doublet;

(vi) all end-products were characterised by microanalysis, NMR and/or mass spectroscopy;

EXAMPLE 1

A stirred mixture of 1-(4-bromophenylsulphonyl)piperidine-4-carboxylic acid (348 mg) and thionyl chloride (2 ml) was heated under reflux for 3 hours. The excess thionyl chloride was removed by evaporation and the residual solid azeotroped with toluene (2×10 ml).

The acid chloride obtained was dissolved in dicliloromethane (25 ml) and the solution was added over 5 minutes to a stirred solution of 4-(4-pyridyl)piperidine (150 mg) and triethylamine (0.7 ml) in dichloromethane (25 ml) at 25° C. The mixture was stirred for 1 hour. The dichloromethane solution was washed with saturated sodium bicarbonate solution (2×25 ml) and saturated brine (1×25 ml), dried and evaporated to give an oil.

The oil was purified by a chromatography on silica gel. Elution with a mixture of dichloromethane/methanol/0.88 ammonia (130:3:1) gave a foam, Trituration with diethyl ether (20 ml) gave, as a colourless solid, 1-(4-bromophenylsulphonyl)-4-[4-(4-pyridyl)piperidine-1-ylcarbonyl]piperidine: mp 154–5° C.: microanalysis, found: C, 53.3; H, 5.6; N, 8.6%; $C_{22}H_{26}BrN_3O_3S$ requires: C, 53.7; H, 5.3; N, 8.5%; NMR ($CDCl_3$): 1.42–1.64(m, 2H), 1.72–1.84(m, 2H), 1.84–2.02 (m, 4H), 2.42–2.80(m, 5H), 3.70–3.80(m, 2H), 3.82–3.96(m, 1H), 4.74–4.82(m, 1H), 7.08(d, 2H), 7.60–7.70(m, 4H), 8.54(d, 2H); EI-MS m/z 492 (M+H).

The starting acid was prepared as follows:

A solution of 4-bromophenyl sulphonyl chloride (53.76 g) in dichloromethane (700 ml) was added to a stirred solution of ethyl piperidine-4-carboxylate (32.97 g) in dichloromethane (500 ml) containing triethylamine (36 ml) at 0° C. and under argon over 0.75 hours. The reaction was stirred for 18 hours. The reaction mixture was washed with water (2×500 ml), saturated brine (1×500 ml), dried and evaporated. The residual solid was triturated in isohexane (500 ml) for 1 hour, collected by filtration and dried to give, as a colourless solid, ethyl 1-(4-bromophenylsulphonyl)piperidine-4-carboxylate (79 g); mp 132–3° C.; NMR ($CDCl_3$): 1.21(t, 3H), 1.70–1.90(m, 2H), 1.90–2.05(m, 2H), 2.18–2.33(m, 1H), 2.45–2.60(m, 2H), 3.53–3.67(m, 2H), 4.10(q, 2H), 7.55–7.70(m, 4H); EI-MS m/z 376 (M+H).

Sodium hydroxide solution (100 ml at 40% w/v) was added to a stirred suspension of the above ester (78.0 g) in ethanol (200 ml)/water (100 ml). Water (100 ml) was added and the reaction mixture heated to reflux and reflux maintained for 30 minutes. The reaction mixture was cooled and the crystalline sodium salt was collected. This sodium salt was suspended in water (350 ml) and glacial acetic acid added to adjust the pH of the solution to 5. The mixture was stirred for 1 hour and the colourless solid collected, washed with water and dried to give, as a colourless solid, 1-(4-bromophenylsulphonyl)piperidine-4-carboxylic acid (68.4 g): m.p. 225–227° C.; microanalysis, found: C, 41.0; H, 3.7; N, 3.9%; $C_{12}H_{14}BrNO_4S$ requires: C, 41.4; H, 4.1; N 4.0%; NMR: 1.41–1.63(m, 2H), 1.73–1.93(m, 2H), 2.11–2.30(m, 1H), 2.44(t, 2H); 3.28–3.60(m, 2H), 7.62(d, 2H) 7.89(d, 2H).

EXAMPLE 2

4-(4-Pyridyl)piperidine (170 mg) was added to a stirred solution of 1-(4-nitrophenoxycarbonyl)-4-(4-bromophenylsulphonyl)piperazine (470 mg) in dimethylformamide (10 ml) at 25° C. under an argon atmosphere. The reaction mixture was heated to 100–105° C. for 18 hours. After cooling, water (55 ml) was added and the aqueous phase was extracted with ethyl acetate (3×30 ml). The combined organic phases were washed with 1M sodium hydroxide (3×15 ml), water (3×20 ml) and saturated brine (1×40 ml), dried and evaporated to give a solid.

The solid was purified by chromatography on silica gel. Elution with a mixture of dichloromethane/methanol/0.88 ammonia (130:3:1) gave, as a colourless solid, 1-(4-bromophenylsulphonyl)-4-(4-pyridyl)piperidine-1-ylcarbonyl)piperazine (211 mg): mp 202–203° C.; microanalysis, found: C, 51.1; H, 4.7; H, 11.4%; $C_{21}H_{25}BrN_4O_3S$ requires: C. 51.2; H, 5.1; N, 11.6%; NMR ($CDCl_3$): 1.55–1.77(m, 2H), 1.80–1.92(m, 2H), 2.59–2.72 (m, 1H), 2.80–2.92(t,d, 2H), 3.04(t, 4H), 3.38(t, 4H), 3.78 (bd, 2H), 7.10(d, 2H), 7.61(d, 2H), 7.70(d,2H), 8.55(d, 1H); MS: m/z 493 (M+H).

The starting piperazine derivative was prepared as follows:

4-Nitrophenyl chloroformate (1.005 g) was added to a stirred solution of 4-bromophenylsulphonylpiperazine (1.52 g) and triethylamine (1.1 ml) in dichloromethane (75 ml) at 0° C. The resulting solution was stirred at 0° C. for 2 hours and then at 25° C. for 16 hours. The organic phase was washed with 1M sodium hydroxide solution (3×5 ml) and saturated brine (3×20 ml), dried and evaporated to give a foam.

The foam was purified by chromatography on silica gel. Elution with dichloromethane gave, as a colourless solid, 1-(4-nitrophenyloxycarbonyl)-4-(4-bromophenylsulphonyl)piperazine (873 mg): NMR ($CDCl_3$): 3.10(t, 4H), 3.63–3.82 (bd, 4H), 7.21 (d, 2H), 7.61(d, 2H), 7.71(d, 2H), 8.22(d, 2H); EI-MS m/z 469 ($M^+$).

EXAMPLE 3

4-Chlorophenylsulphonyl chloride (425 mg) in dichloromethane (15 mL) was added dropwise over 5 minutes to a stirred solution of 1-[4-(4-pyridyl)-1-piperidine-1-ylcarbonyl]piperazine (548 mg) and triethylamine (0.45 mL) in dichloromethane (10 mL) at 20° C. The mixture stirred for 1 hour and the organic phase was washed with water, saturated brine solution, dried and evaporated. The residue was crystallised from ethyl acetate to give, as a cream-coloured solid, 1-(4-chlorophenylsulphonyl)-4-[4-(4-pyridyl)piperidine-1-ylcarbonyl]piperazine (649 mg): m.p. 234–235°: microanalysis: found C, 56.0; H, 5.8; N, 12.8; S 7.2%: $C_{21}H_{25}N_4ClO_3S$ requires: C, 56.1; H, 5.6; H, 12.5, S 7.2%: NMR ($CDCl_3$): 1.52–1.7(m, 2H), 1.78–1.88(m, 2H), 2.58–2.72(m, 1H), 2.79–2.93(td,2h), 3.02(t, 4H), 3.38(t, 4H), 3.78(d, 2H), 7.08(d, 2H), 7.48(d, 2H), 7.65(d, 2H), 8.52(d, 21H), EI-MS m/z 449(M+H).

The starting materials for the above compound were prepared as follows:

A mixture of 4,4'-bipyridyl (20 g) in water (330 mL) was hydrogenated at 5 atmospheres pressure and at 50° C. over 5% Rh-C catalyst (5.0 g).

The uptake of hydrogen gas was continued until the thermatical amount of hydrogen had been absorbed. After cooling, the catalyst was removed by filtration through celite. The water was evaporated and the residue azeotroped with toluene (2×100 mL). The residue was purified by chromatography on neutral alumina using a mixture of dichloromethane-methanol (98:2) as eluent to give, as a cream-coloured solid, 4-(4-pyridyl)piperazine (11.4 g): m.p. 82–84° C.: NMR (CDCl$_3$); 1.57–1.70(qd, 2H), 1.82(m, 2h), 2.53–2.63(ttt, 1H), 2.68–2.80 (td, 2H), 3.20 (d, 2H), 7.12(d, 2H), 8.52(d, 2H); EI-MS m/z 163 (M+H).

4-(4-Pyridyl)piperidine (2.44 g) was added to a stirred suspension of 1-t-butoxycarbonyl-4-(4-nitrophenoxycarbonyl)piperazine (5.26 g) in dimethylformamide (90 mL) at 25° C. The reaction mixture was heated at 105° C. for 18 hours. The dimethylformamide was evaporated and water (500 mL) added, The aqueous phase was extracted with ethyl acetate. The organic phase was washed with 1M sodium hydroxide solution (5×100 mL) and saturated brine (2×100 mL), dried and evaporated, The residue was purified by chromatography on silica gel using a mixture of dichloromethane: methanol: 0.88 ammonia (94:5:1) as eluent to give a yellow oil. Trituration with ether gave, as a pale yellow solid, 1-t-butoxycarbonyl-4-[4-(4-pyridyl)-1-piperidylcarbonyl]piperazine (2.62 g); mp 143–4° C.; NMR (CDCl$_3$) 1.44(s, 9H), 1.58–1.78(m, 2H), 1.78–1.92(d, 2H), 2.60–2.75(m, 1H), 2.80–2.96 (m, 2H), 3.92–3.25(t, 4H), 3.38–3.50(m, 4H), 3.82(d, 2H), 7.10(d, 2H), 8.51(d, 2H); EI-MS m/z 375(M+H).

1-[4-(4-pyridyl)piperidine-1-ylcarbonyl]piperazine

Trinfluoroacetic acid (6 mL) was added slowly a solution of the above t-butoxycarbonyl derivative (2.62 g) in dichloromethane (20 mL) at 20° C. The reaction mixture was stirred for 5 hours at 20° C. The excess trifluoroacetic acid and solvent were evaporated. The residue was treated with saturated brine solution (25 mL) and 5M sodium hydroxide solution added to pH12. The aqueous phase was extracted with dichloromethane (6×30 mL). The combined organic phases were washed with saturated brine (2×25 mL), dried and evaporated to give, as a yellow solid, 1-[4-(4-pyridyl)-1-piperidylcarbonyl]piperazine 91.90 g); m.p. 116–117° C.: NMR (CDCl$_3$) 1.60–1.79(m, 2H), 1.80–1.94(m, 2H), 2.58–2.76(m, 1H), 2.80–2.98(m, 6H), 3.17–3.28(t, 4H), 3.75–3.84(d, 2H), 7.10(d, 2H), 8.51(dd, 2H).

EXAMPLE 4

A solution of 4-trifluoromethylphenylsulphonyl chloride (394 mg) in methylene chloride (4 ml) was added dropwise over 15 minutes to a mixture of 1-(4-piperidinylmethyl)-4-(4-pyridyl)piperidine hydrochloride (550 mg) and triethylamine (1.07 ml) in dichloromethane (10 ml) at 0° C. The solution was stirred at ambient temperature for 18 hours. The solution was diluted with dichloromethane and washed with water, dried (Na$_2$SO$_4$) and evaporated. The residue was purified by chromatography eluting with 2% methanol in dichloromethane. Recrystallisation from ethyl acetate/hexane gave, as a solid 1-[1-(4-trifluoromethylphenylsulphonyl)-(4-piperidinylmethyl)]-4-(4-pyridyl)piperidine (395 mg): NMR (CDCl$_3$): 1.30 (m, 2H), 1.45 (m, 1H), 1.80 (m, 6H), 2.00 (dt, 2H), 2.20 (d, 2H), 2.30 (dt, 2H), 2.40 (m, 2H), 2.90 (d, 2H), 3.80 (d, 2H), 7.10 (d, 2H), 7.80 (d, 2H), 8.50 (d, 2H); m/z 468 (M+1).

The starting material was prepared as follows:

To a solution of N-tert-butoxycarbonyl isonipecotic acid (7.20 g) and N,O-dimethylhydroxylamine hydrochloride (3.68 g) in dichloromethane (100 ml) was added 1-(3-dimethylaminopropyl)-3-ethylcarbodiimide hydrochloride (7.23 g), N-hydroxybenzotriazole (5.10 g) and triethylamine (10.52 ml). The resulting solution was stirred at ambient temperature for 18 hours. The solution was diluted with dichloromethane and washed with water, 2M aqueous citric acid solution, saturated aqueous sodium bicarbonate solution, dried (Na$_2$SO$_4$) and evaporated to give 1-(tert-butoxycarbonyl)-4-(N,O-dimethylhydroxylamino carbonyl) piperidine (8.01 g) as an oil: NMR (CDCl$_3$): 1.40 (s, 9H), 1.70 (m, 4H), 2.80 (m, 3H), 3.20 (s, 31) 3.70 (s, 31H), 4.20 (m, 21H); m/z 273 (M+1).

To a solution of 1-(tert-butoxycarbonyl)-4-(N,O-dinmethylhydroxylamino carbonyl)piperidine (8.00 g) in tetrahydrofuran (150 ml) at 0° C. was added lithium aluminum hydride (1.23 g) portionwise over 5 minutes. The resulting suspension was stirred at 0° C. for 3 hours and then water (1 ml), 2M aqueous sodium hydroxide solution (1 ml) and water (4 ml) were added and the suspension filtered through celite. The filter cake was washed with dichloromethane and the combined organic extracts evaporated to give 1-(tert-butoxycarbonyl)-4-(formyl)piperidine (7.04 g) as an oil: NMR (CDCl$_3$): 1.40 (s, 9H), 1.60 (m, 2H), 2.40 (m, 1H), 2.90 (m. 2H), 3.40 (d, 1H), 4.00 (m, 3H), 9.70 (s, 1H).

To a solution of 1-(tert-butoxycarbonyl)-4-(formyl) piperidine (2.59 g) and 4-(4-pyridyl)piperidine (1.97 g) in methanol/acetic acid (99:1) (50 ml) was added sodium cyanoborohydride (2.29 g) portionwise over 30 minutes and the resultant suspension stirred at ambient temperature for 3 hours. The suspension was quenched by addition of saturated aqueous sodium bicarbonate and the resulting mixture extracted with ethyl acetate. The organic phase was dried (Na$_2$SO$_4$) and evaporated, The residue was purified by chromatography eluting with 5% methanol in dichloromethane to give 1-[1-tert-butoxycarbonyl(4-piperidinylmethyl)]-4-(4-pyridyl)piperidine (1.65 g) as a solid: NMR (CDCl$_3$): 1.10 (m, 2H), 1.40 (s, 9H), 1.75 (m, 7H), 2.00 (dt, 2H), 2.20 (d, 2H), 2.45 (m, 1H), 2.70 (m, 2H), 3.00 (d, 2H), 4.10 (m, 2H), 7.20 (d, 2H), 8.50 (d, 2H); m/z 360 (M+1).

Ethyl acetate saturated with gaseous HCl (50 ml) was added to a solution of 1-[1-tert-butoxycarbonyl(4-piperidinylmethyl)]-4-(4-pyridyl)piperidine (1.65 g) in ethyl acetate (15 ml) and the resulting suspension stirred at ambient temperature for 2 hours. Solvent was evaporated to give 1-(4-piperidinylmethyl)4-(4-pyridyl)piperidine hydrochloride (1.70 g) as a yellow hygroscopic foam: NMR (d6-DMSO): 1.40 (m, 2H), 2.00 (m, 4H). 2.20 (m, 1H), 2.40 (m, 1H), 2.80 (m, 2H), 3.00 (m, 4H), 3.20 (m, 4H), 3.60 (d, 2H), 7.85 (d, 2H), 8.80 (d, 2H): m/z 260 (M+1).

EXAMPLE 5

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| | mg/tablet |
|---|---|
| (a) Tablet I | |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium Stearate | 1.0 |
| (b) Tablet II | |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| | mg/capsule |
|---|---|
| (d) Capsule | |
| Compound Z* | 10 |
| Lactose Ph. Eur. | 488.5 |
| Magnesium stearate | 1.5 |

Note
*The active ingredient Compound Z is a compound of formula I or Ia, or a pharmaceutically-acceptable salt thereof, for example a compound of formula I described in any of the preceeding Examples.

The tablet compositions (a)–(c) may be enteric coated by conventional means, for example, with cellulose acetate phthalate.

Scheme 1

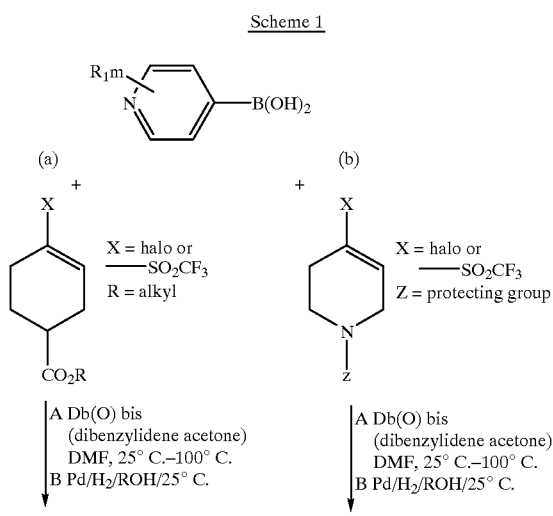

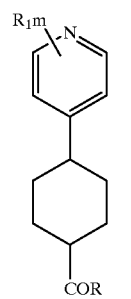

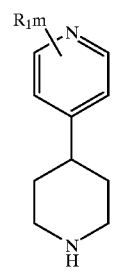

FORMULAE

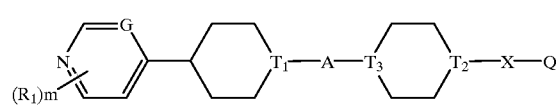

Ia

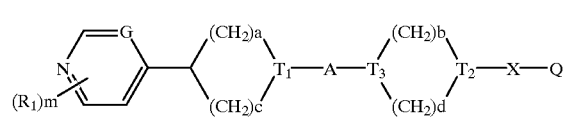

I

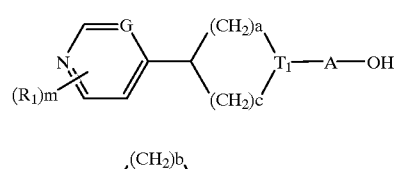

II

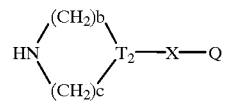

III

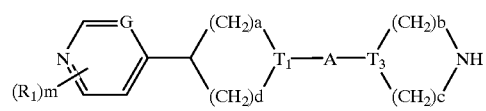

IV

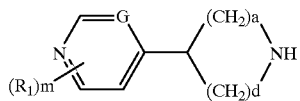

V

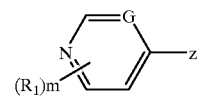

VI

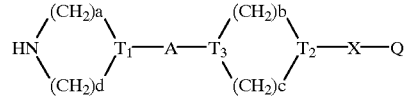

VII

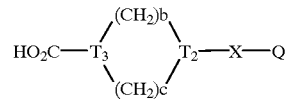

VIII

What is claimed is:

1. A compound of formula I

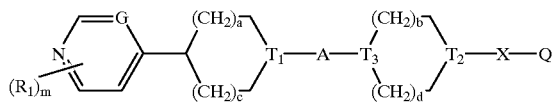

(I)

wherein: G is CH; $T_1$ is N; $T_2$ is N; $T_3$ is N; a and b are 2; c and d are 2;

wherein the ring containing $T_1$ and the ring containing $T_2$ may, independently, be optionally substituted by one or more substituents selected from (1–6C)alkyl, (1–6C)alkoxy, phenyl(1–4C)alkyl, halogeno and (1–6C)alkoxycarbonyl;

A is selected from (1–4C)alkylene, carbonyl or (1–4C)alkylcarbonyl;

X is selected from oxy, thio, sulphinyl, sulphonyl, carbonyl, carbonylamino, N-(1–6C)alkylcarbonylamino, sulphonylamino, methylene, (1–4C)alkymethylene and di-(1–6C)alkylmethylene;

Q is selected from (5–7C)cycloalkyl, a heterocyclic moiety containing up to 4 heteroatoms selected from nitrogen, oxygen and sulphur; phenyl, naphthyl, phenyl (1–4C)alkyl and phenyl(2–6C)alkenyl, and wherein the last three groups may optionally bear a phenyl substituent;

wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N-[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl, tetrazolyl and a heteroaryl group comprising of 5- or 6-membered monocyclic ring containing up to three heteroatoms selected from nitrogen, oxygen and sulphur;

$R^1$ is hydrogen, amino, halogeno, cyano, nitro, carboxy, (1–6C)alkanoyl, (1–6C)alkyl, (1–6C)alkoxy, N-(1–6C)alkylamino, N,N-di-[(1–6C)alkyl]amino, (1–6C)alkylthio, (1–6C)alkylsulphinyl and (1–6C)alkylsulphonyl; and m is 1 or 2;

or a pharmaceutically-acceptable salt thereof.

2. A compound of formula I, or a pharmaceutically-acceptable salt thereof, as claimed in claim 1 wherein X is sulphonyl.

3. A compound of formula I, or a pharmaceutically-acceptable salt thereof, as claimed in claim 1 or claim 2, wherein A is carbonyl.

4. A compound of formula I, or a pharmaceutically-acceptable salt thereof, as claimed in claim 1 or claim 2, wherein the heterocyclic rings containing $T_1$ and $T_2$ are unsubstituted.

5. A compound of formula I, or a pharmaceutically-acceptable salt thereof, as claimed in claim 1 or claim 2, wherein Q is naphthyl.

6. A pharmaceutical composition comprising a compound of formula I, or a pharmaceutically-acceptable salt thereof as claimed in claim 1 or claim 2, and at least one pharmaceutically-acceptable diluent or carrier.

7. A method for the treatment of a medical condition mediated in whole or in part by the inhibition of oxido-squalene cyclase in a warm-blooded animal in need thereof, comprising administering to said animal an oxido-squalene cyclase inhibiting-effective amount of a compound as claimed in claim 1 or claim 2, or a pharmaceutically-acceptable salt thereof.

8. A method for the inhibition of cholesterol biosynthesis in a warm-blooded animal in need thereof, comprising administering to said animal a cholesterol biosynthesis inhibiting-effective amount of a compound as claimed in claim 1 or claim 2, or a pharmaceutically-acceptable salt thereof.

9. A method for the treatment of hypercholesterolemia in a warm-blooded animal in need there of, comprising administering to said animal a hypercholesterolemia treatment-effective amount of a compound as claimed in claim 1 or claim 2, or a pharmaceutically-acceptable salt thereof.

10. A method for the treatment of an ischaemic disease associated with atheromatous vascular degeneration in a warm-blooded animal in need thereof, comprising administering to said animal a treatment-effective amount as claimed in a compound of claim 1 or claim 2, or a pharmaceutically-acceptable salt thereof.

11. The method of claim 10 wherein said ischaemic disease is atherosclerosis.

* * * * *